United States Patent
Chung et al.

(10) Patent No.: US 8,969,296 B2
(45) Date of Patent: Mar. 3, 2015

(54) TGFP-CAP PEPTIDE AND ITS USES

(75) Inventors: Yong-Ji Chung, Yongin-si (KR); Young Deug Kim, Sihung-si (KR); Eun Mi Kim, Jeollanam-do (KR); Jun Young Choi, Gunpo-si (KR); Jin Seuk Kim, Seoul (KR); Sang Su Song, Seoul (KR); Kyoung Mi Cho, Cheonan-si (KR)

(73) Assignee: Caregen Co., Ltd, Gunpo-si, Gyeonggi-do (KR)

( * ) Notice: Subject to any disclaimer, the term of this patent is extended or adjusted under 35 U.S.C. 154(b) by 1304 days.

(21) Appl. No.: 12/596,479

(22) PCT Filed: Sep. 12, 2007

(86) PCT No.: PCT/KR2007/004405
§ 371 (c)(1),
(2), (4) Date: Dec. 21, 2009

(87) PCT Pub. No.: WO2008/130082
PCT Pub. Date: Oct. 30, 2008

(65) Prior Publication Data
US 2010/0160238 A1  Jun. 24, 2010

(30) Foreign Application Priority Data

Apr. 19, 2007  (KR) .................. 10-2007-0038531

(51) Int. Cl.
| | |
|---|---|
| *A61K 8/64* | (2006.01) |
| *C07K 7/08* | (2006.01) |
| *A61K 38/00* | (2006.01) |
| *C07K 14/495* | (2006.01) |
| *A61K 38/18* | (2006.01) |
| *A61Q 19/02* | (2006.01) |

(52) U.S. Cl.
CPC ........... *C07K 14/495* (2013.01); *A61K 38/1841* (2013.01); *A61K 8/64* (2013.01); *A61Q 19/02* (2013.01); *C07K 7/08* (2013.01); *A61K 38/00* (2013.01)

USPC .............. 514/8.9; 514/1.9; 514/16.7; 424/62; 530/326; 530/327; 530/328

(58) Field of Classification Search
None
See application file for complete search history.

(56) References Cited

U.S. PATENT DOCUMENTS 7,618,943 B2 * 11/2009 Berdel et al. .................. 514/1.1
2007/0099840 A1 * 5/2007 Ulijn et al. ..................... 514/17

FOREIGN PATENT DOCUMENTS

WO  WO 03/093293 A2 * 11/2003
WO  WO 2006/012355 A1 * 2/2006 ............. A61K 51/00

OTHER PUBLICATIONS

Thermo Electron Corporation, "N-Terminal Acetylation and C-Terminal Amidation of Peptides", two pages (2004) retrieved from http://www.thermo.com/eThermo/CMA/PDFs/Various/File_24805.pdf on Mar. 21, 2013.*

* cited by examiner

*Primary Examiner* — Christine Foster
(74) *Attorney, Agent, or Firm* — Clark & Elbing LLP

(57) ABSTRACT

The present invention relates to a GFP-CAP peptide having an amino acid sequence derived from TGF-β1 (transforming growth factor-β1) and a cell adhesion sequence, wherein the amino acid sequence derived from TGF-β1 consists of the amino acid sequence of SEQ ID NO:1 and the TGFP-CAP peptide is represented by the following formula I: Ile-Trp-Ser-Leu-Asp-Thr-Gln-Tyr-Cell adhesion sequence (I). The TGFP-CAP peptide of the present invention exhibits excellent anti-angiogenic activity. In addition, the TGFP-CAP peptide of the present invention prevents effectively melanin generation in skin to have skin whitening effects. The present peptide shows much higher stability and permeability to skin than natural-occurring TGF-β1. Such plausible activities and safety of the present peptide enable advantageously to application to drugs, quasi-drugs and cosmetics.

6 Claims, 9 Drawing Sheets control

PD98059

TGFb1 + PD98059

TGP2 + PD98059

SEQUENCE LISTING

<160> NUMBER OF SEQ ID NOS: 33

<210> SEQ ID NO 1
<211> LENGTH: 8
<212> TYPE: PRT
<213> ORGANISM: Artificial Sequence
<220> FEATURE:
<223> OTHER INFORMATION: TGF-beta 1 derived sequence

<400> SEQUENCE: 1

Ile Trp Ser Leu Asp Thr Gln Tyr
1               5

<210> SEQ ID NO 2
<211> LENGTH: 13
<212> TYPE: PRT
<213> ORGANISM: Artificial Sequence
<220> FEATURE:
<223> OTHER INFORMATION: TGF-CAP peptide

<400> SEQUENCE: 2

Ile Trp Ser Leu Asp Thr Gln Tyr Gly Gly Arg Gly Asp
1               5                   10

<210> SEQ ID NO 3
<211> LENGTH: 3
<212> TYPE: PRT
<213> ORGANISM: Artificial Sequence
<220> FEATURE:
<223> OTHER INFORMATION: Cell adhesion sequence_RGD

<400> SEQUENCE: 3

Arg Gly Asp
1

<210> SEQ ID NO 4
<211> LENGTH: 4
<212> TYPE: PRT
<213> ORGANISM: Artificial Sequence
<220> FEATURE:
<223> OTHER INFORMATION: Cell adhesion sequence_RGDS

<400> SEQUENCE: 4

Arg Gly Asp Ser
1

<210> SEQ ID NO 5
<211> LENGTH: 4
<212> TYPE: PRT
<213> ORGANISM: Artificial Sequence
<220> FEATURE:
<223> OTHER INFORMATION: Cell adhesion sequence_RGDC

<400> SEQUENCE: 5

Arg Gly Asp Cys
1

<210> SEQ ID NO 6
<211> LENGTH: 4
<212> TYPE: PRT
<213> ORGANISM: Artificial Sequence
<220> FEATURE:
<223> OTHER INFORMATION: Cell adhesion sequence_RGDV

<400> SEQUENCE: 6

Arg Gly Asp Val
1

```
<210> SEQ ID NO 7
<211> LENGTH: 4
<212> TYPE: PRT
<213> ORGANISM: Artificial Sequence
<220> FEATURE:
<223> OTHER INFORMATION: Cell adhesion sequence_RGES

<400> SEQUENCE: 7

Arg Gly Glu Ser
1

<210> SEQ ID NO 8
<211> LENGTH: 10
<212> TYPE: PRT
<213> ORGANISM: Artificial Sequence
<220> FEATURE:
<223> OTHER INFORMATION: Cell adhesion sequence_RGDSPASSKP

<400> SEQUENCE: 8

Arg Gly Asp Ser Pro Ala Ser Ser Lys Pro
1               5                   10

<210> SEQ ID NO 9
<211> LENGTH: 5
<212> TYPE: PRT
<213> ORGANISM: Artificial Sequence
<220> FEATURE:
<223> OTHER INFORMATION: Cell adhesion sequence_GRGDS

<400> SEQUENCE: 9

Gly Arg Gly Asp Ser
1               5

<210> SEQ ID NO 10
<211> LENGTH: 6
<212> TYPE: PRT
<213> ORGANISM: Artificial Sequence
<220> FEATURE:
<223> OTHER INFORMATION: Cell adhesion sequence_GRADSP

<400> SEQUENCE: 10

Gly Arg Ala Asp Ser Pro
1               5

<210> SEQ ID NO 11
<211> LENGTH: 4
<212> TYPE: PRT
<213> ORGANISM: Artificial Sequence
<220> FEATURE:
<223> OTHER INFORMATION: Cell adhesion sequence_KGDS

<400> SEQUENCE: 11

Lys Gly Asp Ser
1

<210> SEQ ID NO 12
<211> LENGTH: 6
<212> TYPE: PRT
<213> ORGANISM: Artificial Sequence
<220> FEATURE:
<223> OTHER INFORMATION: Cell adhesion sequence_GRGDSP

<400> SEQUENCE: 12

Gly Arg Gly Asp Ser Pro
1               5
```

-continued

```
<210> SEQ ID NO 13
<211> LENGTH: 6
<212> TYPE: PRT
<213> ORGANISM: Artificial Sequence
<220> FEATURE:
<223> OTHER INFORMATION: Cell adhesion sequence_GRGDTP

<400> SEQUENCE: 13

Gly Arg Gly Asp Thr Pro
1               5

<210> SEQ ID NO 14
<211> LENGTH: 5
<212> TYPE: PRT
<213> ORGANISM: Artificial Sequence
<220> FEATURE:
<223> OTHER INFORMATION: Cell adhesion sequence_GRGES

<400> SEQUENCE: 14

Gly Arg Gly Glu Ser
1               5

<210> SEQ ID NO 15
<211> LENGTH: 7
<212> TYPE: PRT
<213> ORGANISM: Artificial Sequence
<220> FEATURE:
<223> OTHER INFORMATION: Cell adhesion sequence_GRGDSPC

<400> SEQUENCE: 15

Gly Arg Gly Asp Ser Pro Cys
1               5

<210> SEQ ID NO 16
<211> LENGTH: 6
<212> TYPE: PRT
<213> ORGANISM: Artificial Sequence
<220> FEATURE:
<223> OTHER INFORMATION: Cell adhesion sequence_GRGESP

<400> SEQUENCE: 16

Gly Arg Gly Glu Ser Pro
1               5

<210> SEQ ID NO 17
<211> LENGTH: 4
<212> TYPE: PRT
<213> ORGANISM: Artificial Sequence
<220> FEATURE:
<223> OTHER INFORMATION: Cell adhesion sequence_SDGR

<400> SEQUENCE: 17

Ser Asp Gly Arg
1

<210> SEQ ID NO 18
<211> LENGTH: 5
<212> TYPE: PRT
<213> ORGANISM: Artificial Sequence
<220> FEATURE:
<223> OTHER INFORMATION: Cell adhesion sequence_YRGDS

<400> SEQUENCE: 18

Tyr Arg Gly Asp Ser
1               5
```

```
<210> SEQ ID NO 19
<211> LENGTH: 15
<212> TYPE: PRT
<213> ORGANISM: Artificial Sequence
<220> FEATURE:
<223> OTHER INFORMATION: Cell adhesion sequence_GQQHHLGGAKQAGDV

<400> SEQUENCE: 19

Gly Gln Gln His His Leu Gly Gly Ala Lys Gln Ala Gly Asp Val
1               5                   10                  15

<210> SEQ ID NO 20
<211> LENGTH: 3
<212> TYPE: PRT
<213> ORGANISM: Artificial Sequence
<220> FEATURE:
<223> OTHER INFORMATION: Cell adhesion sequence_GPR

<400> SEQUENCE: 20

Gly Pro Arg
1

<210> SEQ ID NO 21
<211> LENGTH: 3
<212> TYPE: PRT
<213> ORGANISM: Artificial Sequence
<220> FEATURE:
<223> OTHER INFORMATION: Cell adhesion sequence_GHK

<400> SEQUENCE: 21

Gly His Lys
1

<210> SEQ ID NO 22
<211> LENGTH: 5
<212> TYPE: PRT
<213> ORGANISM: Artificial Sequence
<220> FEATURE:
<223> OTHER INFORMATION: Cell adhesion sequence_YIGSR

<400> SEQUENCE: 22

Tyr Ile Gly Ser Arg
1               5

<210> SEQ ID NO 23
<211> LENGTH: 5
<212> TYPE: PRT
<213> ORGANISM: Artificial Sequence
<220> FEATURE:
<223> OTHER INFORMATION: Cell adhesion sequence_PDSGR

<400> SEQUENCE: 23

Pro Asp Ser Gly Arg
1               5

<210> SEQ ID NO 24
<211> LENGTH: 9
<212> TYPE: PRT
<213> ORGANISM: Artificial Sequence
<220> FEATURE:
<223> OTHER INFORMATION: Cell adhesion sequence_CDPGYIGSR

<400> SEQUENCE: 24

Cys Asp Pro Gly Tyr Ile Gly Ser Arg
1               5
```

```
<210> SEQ ID NO 25
<211> LENGTH: 4
<212> TYPE: PRT
<213> ORGANISM: Artificial Sequence
<220> FEATURE:
<223> OTHER INFORMATION: Cell adhesion sequence_LCFR

<400> SEQUENCE: 25

Leu Cys Phe Arg
1

<210> SEQ ID NO 26
<211> LENGTH: 3
<212> TYPE: PRT
<213> ORGANISM: Artificial Sequence
<220> FEATURE:
<223> OTHER INFORMATION: Cell adhesion sequence_EIL

<400> SEQUENCE: 26

Glu Ile Leu
1

<210> SEQ ID NO 27
<211> LENGTH: 5
<212> TYPE: PRT
<213> ORGANISM: Artificial Sequence
<220> FEATURE:
<223> OTHER INFORMATION: Cell adhesion sequence_EILDV

<400> SEQUENCE: 27

Glu Ile Leu Asp Val
1               5

<210> SEQ ID NO 28
<211> LENGTH: 8
<212> TYPE: PRT
<213> ORGANISM: Artificial Sequence
<220> FEATURE:
<223> OTHER INFORMATION: Cell adhesion sequence_EILDVPST

<400> SEQUENCE: 28

Glu Ile Leu Asp Val Pro Ser Thr
1               5

<210> SEQ ID NO 29
<211> LENGTH: 8
<212> TYPE: PRT
<213> ORGANISM: Artificial Sequence
<220> FEATURE:
<223> OTHER INFORMATION: Cell adhesion sequence_EILEVPST

<400> SEQUENCE: 29

Glu Ile Leu Glu Val Pro Ser Thr
1               5

<210> SEQ ID NO 30
<211> LENGTH: 3
<212> TYPE: PRT
<213> ORGANISM: Artificial Sequence
<220> FEATURE:
<223> OTHER INFORMATION: Cell adhesion sequence_LDV

<400> SEQUENCE: 30

Leu Asp Val
1
```

-continued

```
<210> SEQ ID NO 31
<211> LENGTH: 5
<212> TYPE: PRT
<213> ORGANISM: Artificial Sequence
<220> FEATURE:
<223> OTHER INFORMATION: Cell adhesion sequence_LDVPS

<400> SEQUENCE: 31

Leu Asp Val Pro Ser
1               5

<210> SEQ ID NO 32
<211> LENGTH: 19
<212> TYPE: PRT
<213> ORGANISM: Artificial Sequence
<220> FEATURE:
<223> OTHER INFORMATION: TGF-beta 1 derived sequence
<220> FEATURE:
<221> NAME/KEY: misc_feature
<222> LOCATION: (11)..(16)
<223> OTHER INFORMATION: Xaa is Gly and any one or more of Xaa can be
      present or absent

<400> SEQUENCE: 32

Ile Trp Ser Leu Asp Thr Gln Tyr Gly Gly Xaa Xaa Xaa Xaa Xaa Xaa
1               5                   10                  15

Arg Gly Asp

<210> SEQ ID NO 33
<211> LENGTH: 8
<212> TYPE: PRT
<213> ORGANISM: Artificial Sequence
<220> FEATURE:
<223> OTHER INFORMATION: TGF-beta 1 derived sequence

<400> SEQUENCE: 33

Ile Trp Ser Leu Asp Thr Gln Tyr
1               5
```

TGFP-CAP PEPTIDE AND ITS USES

CROSS-REFERENCE TO RELATED APPLICATIONS

This application claims priority under 35 U.S.C. §371 from international application PCT/KR2007/004405, filed Sep. 12, 2007, which claims priority from Korean Patent Application 10-2007-0038531, filed Apr. 19, 2007.

BACKGROUND OF THE INVENTION

1. Field of the Invention

The present invention relates to novel peptides comprising TGF-β-originated peptides and their uses.

2. Description of the Related Art

Transforming growth factor-beta (TGF-β) is a group of polypeptide growth factors regulating cell division and differentiation. This group also includes Mulleria inhibitor (Cate et al., 1986, Cell, 45:685-698), inhibins (Mason et al., 1985, Nature, 318:659-663), and Drosophilla DPP-C (decapentaplegic gene complex) protein (Padgett et al., 1987, Nature, 325:81-84). TGF-β consists of two similar disulfide-linked subunits each having a molecular weight of 13,000 daltons (Assoian et al., 1983, J. Biol. Chem. 258:7155-7160; Frolik et al., 1983, Proc. Natl. Acad. Sci. USA 80:3676-3680; Frolik et al., 1984, J. Biol. Chem. 260:10995-11000). TGF-β has been isolated from several tissues, including placenta (Frolik et al., 1983, Nature 325:81-84), human platelet (Childs et al., 1982, Proc. Natl. Acad. Sci. USA 79:5312-5316, Assioan et al., 1983, J. Biol. Chem. 258:7155-7160), kidney (Roberts et al., 1983, Biochemistry 22:5692-5698), and bovine demineralized bone (Seyedin et al., 1985, Proc. Natl. Acad. Sci. USA 82:119-123).

TGF-β is able to increase anchorage-independent growth of normal rat kidney fibroblast in the presence of 10% serum and epidermal growth factor (Roberts et al., 1981, Proc. Natl. Acad. Sci. USA 78:5339-5343; Roberts et al., 1982, Nature 295:417-419; Twardzik et al., 1985, J. Cell Biochem. 28:289-297), and to induce colonies of AKR-2B fibroblast in only 10% serum (Tucker et al., 1983, Cancer Res. 43:1518-1586). Also, it could cause differentiation of muscle mesenchymal cells and generation of cartilage-specific macromolecules in fetal rats (Seyedin et al., 1986, J. Biol. Chem, 261:5693-5695). In contrast to the positive effects on cell proliferation, not only function-related proteins isolated from African green monkey kidney epithelial cells (BSC-1) but TGF-β purified from human platelet could inhibit cell growth during cell culture (Tucker et al., 1984, Science 226:705-707). In addition, TGF-β inhibits the growth of some human tumor cells (Roberts et., 1985, Proc. Natl. Acad. Sci. USA 82:119-123). These inhibitory or stimulatory effects of TGF-βs have been reported to be dependent on several factors such as cell morphology and cell physiological conditions (Spon et al., 1986, Science 232:534).

TGF-β cDNA clones were isolated from human (Derynck et al., 1985, Nature 316:701-705), mouse (Derynck et al., 1986, J. Biol. Chem. 261:4377-4379), and simian virus 40 (Sharples et. al., 1987, DNA 6:239-244). By analyzing their DNA sequences, it was reported that TGF-β was synthesized as a precursor polypeptide, and then spliced to TGF-β monomer. The TGF-β precursor proteins described above exhibit high homology in their amino acid sequences.

Recently it was identified that a protein isolated from bovine demineralized bone was related to TGF-β (Seyedin et al., 1987, J. Biol. Chem., 262: 1946-1949). It was also isolated from other species, containing porcine blood platelets (Cheifetz et al., 1987, Cell 48:409-415), human prostatic adenocarcinoma cell line PC-3 (Ikeda et al., 1987, Biochemistry 26:2406-2410), and human glioblast cell (Wrann et al., 1987, EMBO 6:1633-1636). Because the partial amino acid sequence of this protein is homologous to that of TGF-β, it was named as TGF-β2. TGF-βs isolated from human (Derynck et al., 1985, Nature 316:701-705), mouse (Derynck et al., 1986, J. Biol. Chem. 261:4377-4379), and simian virus 40 (Sharples et. al., 1987, DNA 6:239-244) were named as TGF-β1.

TGF-β1 is a highly active protein. Unfortunately, its utilization and application have not yet become widened because of its poor expression, high production cost and short half-life.

Throughout this application, various patents and publications are referenced and citations are provided in parentheses. The disclosure of these patents and publications in their entities are hereby incorporated by references into this application in order to more fully describe this invention and the state of the art to which this invention pertains.

DETAILED DESCRIPTION OF THIS INVENTION

The present inventors have made intensive researches to provide novel peptides having skin whitening effects and much higher stability and skin penetration potential than natural-occurring TGF-β1. They have prepared and screened a wide variety of TGF-β1-originated peptides and finally discovered novel peptides with excellent physiological activities and stability, eventually accomplishing the present invention.

Accordingly, it is an object of this invention to provide a novel peptide having TGF-β1-derived peptide sequence.

It is another object of this invention to provide an anti-angiogenic composition.

It is still another object of this invention to provide a skin whitening composition.

It is further object of this invention to provide a method for preventing or treating angiogenesis-associated diseases.

It is still further object of this invention to provide a method for skin whitening.

Other objects and advantages of the present invention will become apparent from the following detailed description together with the appended claims and drawings.

In one aspect of this invention, there is provided a TGFP-CAP peptide having an amino acid sequence derived from TGF-β1 (transforming growth factor-β1) and a cell adhesion sequence, wherein the amino acid sequence derived from TGF-β1 consists of the amino acid sequence of SEQ ID NO:1 and the TGFP-CAP peptide is represented by the following formula I:

Ile-Trp-Ser-Leu-Asp-Thr-Gln-Tyr-Cell adhesion (I)
sequence (SEQ ID NO: 1)

wherein the cell adhesion sequence is RGD(Arg-Gly-Asp (SEQ ID NO:3)), RGDS(Arg-Gly-Asp-Ser (SEQ ID NO:4)), RGDC(Arg-Gly-Asp-Cys (SEQ ID NO:5)), RGDV(Arg-Gly-Asp-Val SEQ ID NO:6)), RGES(Arg-Gly-Glu-Ser (SEQ ID NO:7)), RGDSPASSKP(Arg-Gly-Asp-Ser-Pro-Ala-Ser-Ser-Lys-Pro (SEQ ID NO:8), GRGDS(Gly-Arg-Gly-Asp-Ser (SEQ ID NO:9)), GRADSP(Gly-Arg-Ala-Asp-Ser-Pro (SEQ ID NO:10)), KGDS(Lys-Gly-Asp-Ser (SEQ ID NO:11)), GRGDSP(Gly-Arg-Gly-Asp-Ser-Pro SEQ ID NO:12)), GRGDTP(Gly-Arg-Gly-Asp-Thr-Pro (SEQ ID NO:13), GRGES(Gly-Arg-Gly-Glu-Ser (SEQ ID NO:14)), GRGDSPC(Gly-Arg-Gly-Asp-Ser-Pro-Cys (SEQ ID NO:15)), GRGESP(Gly-Arg-Gly-Glu-Ser-Pro (SEQ ID NO:16)), SDGR(Ser-Asp-Gly-Arg (SEQ ID NO:17)), YRGDS(Tyr-Arg-Gly-Asp-Ser (SEQ ID NO:18)), GQQHHLGGAKQAGDV (Gly-Gln-Gln-His-His-Leu-Gly-Gly-Ala-Lys-Gln-Ala-Gly-Asp-Val (SEQ ID NO:19)), GPR (Gly-Pro-Arg (SEQ ID NO:20)), GHK(Gly-His-Lys SEQ ID NO:21)), YIGSR(Tyr-Ile-Gly-Ser-Arg (SEQ ID NO:22)), PDSGR(Pro-Asp-Ser-Gly-Arg (SEQ ID NO:23)), CDPGYIGSR(Cys-Asp-Pro-Gly-Tyr-Ile-Gly-Ser-Arg (SEQ ID NO:24), LCFR(Leu-Cys-Phe-Arg (SEQ ID NO:25)), EIL (Glu-Ile-Leu (SEQ ID NO:26)), EILDV(Glu-Ile-Leu-Asp-Val (SEQ ID NO:27)), EILDVPST(Glu-Ile-Leu-Asp-Val-Pro-Ser-Thr (SEQ ID NO:28)), EILEVPST(Glu-Ile-Leu-Glu-Val-Pro-Ser-Thr (SEQ ID NO:29)), LDV(Leu-Asp-Val (SEQ ID NO:30)) or LDVPS(Leu-Asp-Val-Pro-Ser (SEQ ID NO:31)).

The present inventors have made intensive researches to provide novel peptides having skin whitening effects and much higher stability and skin penetration potential than natural-occurring TGF-β1. They have prepared and screened a wide variety of TGF-β1-originated peptides and finally discovered novel peptides with excellent physiological activities and stability.

The principle strategies of the present invention are: Firstly, the present peptide is designed to comprise two functional portions, a TGF-β1-originated sequence (i.e., TGF-β1 activity portion) and a cell adhesion sequence. The amino acid sequence of the TGF-β1 activity portion is selected from that of natural-occurring TGF-β1. For enhancing TGF-β1 activity of the present peptide, a cell adhesion sequence is adopted. As results, the TGF-β1 activity portion is composed of Ile-Trp-Ser-Leu-Asp-Thr-Gln-Tyr (SEQ ID NO:1) and the cell adhesion sequence comprises any one of the sequences described above. Since the present peptide constructed by the strategies is a fusion protein of TGF-β1 derived peptide and cell adhesion peptide, it is called as "TGFP (transforming growth factor peptide)-CAP (cell adhesion peptide) peptide".

The cell adhesion sequence in the formula I is a cell adhesion motif. Therefore, it would be obvious to one of skill in the art that longer amino acid sequences comprising the cell adhesion sequence described above fall within the scope of the present invention.

According to a preferred embodiment, the cell adhesion sequence is RGD(Arg-Gly-Asp (SEQ ID NO:3)), RGDS (Arg-Gly-Asp-Ser (SEQ ID NO:4)), RGDC(Arg-Gly-Asp-Cys (SEQ ID NO:5)), RGDV(Arg-Gly-Asp-Val (SEQ ID NO:6)), RGES(Arg-Gly-Glu-Ser (SEQ ID NO:7)), RGDSPASSKP(Arg-Gly-Asp-Ser-Pro-Ala-Ser-Ser-Lys-Pro (SEQ ID NO:8)), GRGDS(Gly-Arg-Gly-Asp-Ser (SEQ ID NO:9)), GRADSP(Gly-Arg-Ala-Asp-Ser-Pro (SEQ ID NO:10)), KGDS(Lys-Gly-Asp-Ser (SEQ ID NO:11)), GRGDSP(Gly-Arg-Gly-Asp-Ser-Pro (SEQ ID NO:12)), GRGDTP(Gly-Arg-Gly-Asp-Thr-Pro (SEQ ID NO:13)), GRGES(Gly-Arg-Gly-Glu-Ser (SEQ ID NO:14)), GRGDSPC(Gly-Arg-Gly-Asp-Ser-Pro-Cys (SEQ ID NO:15)), GRGESP(Gly-Arg-Gly-Glu-Ser-Pro (SEQ ID NO:16)), SDGR(Ser-Asp-Gly-Arg (SEQ ID NO:17)), YRGDS(Tyr-Arg-Gly-Asp-Ser (SEQ ID NO:18)), GQQHHLGGAKQAGDV (Gly-Gln-Gln-His-His-Leu-Gly-Gly-Ala-Lys-Gln-Ala-Gly-Asp-Val (SEQ ID NO:19)) or GPR(Gly-Pro-Arg (SEQ ID NO:20)), most preferably RGD(Arg-Gly-Asp (SEQ ID NO:3)). The RGD sequence is selected from fibronectin as cell matrix proteins.

According to a preferred embodiment, the two functional portions are linked indirectly by linkers. Where linkers are used, the TGFP-CAP peptide is represented by the following formula II:

```
Ile-Trp-Ser-Leu-Asp-Thr-Gln-Tyr-Linker-Cell     (II)
adhesion sequence (SEQ ID NO: 1)
``` wherein the cell adhesion sequence is the same as the formula 1.

A variety of linkers accessible to those of skill in the art may be used as linkers for linking the TGF-β1 activity portion and the cell adhesion portion. Preferably, the linker used in the present invention comprises a plurality of amino acid residues. Linkers comprising amino acid residues are described in Huston, et al., *Methods in Enzymology*, 203:46-88 (1991), and Whitlow, et al., *Protein Eng.*, 6:989 (1993)), the teachings of which are incorporated herein by reference. Linkers useful in the present invention comprise preferably Gly or Gly and Ser residues. Preferable length of linkers ranges from 2 to 18. More preferably, the linker used in the present invention comprises 2-10 Gly residues. Linkers composed of amino acid residues, in particular Gly residues may contribute to stability of the present peptides.

Even though the peptide of this invention per se has higher stability than natural-occurring TGF-β1, its modification enables to show much higher stability. Preferably, the N- or C-terminal of the present peptides represented by the formula I has at least one amino acid residue protected with acetyl group, fluorenyl methoxy carbonyl group, formyl group, palmitoyl group, myristyl group, stearyl group or polyethylene glycol (PEG). The protection groups enhance stability of the present peptides.

Alternatively, the C-terminal of the present peptide is modified with amino group, giving rise to increase in stability of the present peptides.

The term used herein "stability" refers to in vivo stability and storage stability (e.g., storage stability at room temperature) as well. The protection group described above protects the peptides from the attack of protease in vivo.

Most preferably, the TGFP-CAP peptide is represented by the following formula III:

```
Ile-Trp-Ser-Leu-Asp-Thr-Gln-Tyr-Gly(n)-Arg-    (III)
Gly-Asp (SEQ ID NO: 32)
``` wherein n is an integer of 2-8.

An illustrated peptide of the present invention is described in SEQ ID NO:2.

The term used herein "peptide" refers to a linear molecule formed by linking amino acid residues through peptide bonds.

The peptides of the invention may be prepared by conventional chemical synthesis processes known to one of skill in the art, in particular, solid-phase synthesis techniques (Merrifield, *J. Amer. Chem. Soc.* 85:2149-54 (1963); Stewart, et al., *Solid Phase Peptide Synthesis*, 2nd. ed., Pierce Chem. Co.: Rockford, 111 (1984)).

The fundamental structure of the present peptides is a linkage structure of a TGF-β1 derived sequence and a cell adhesion sequence. In this connection, it could be recognized by those of skill in the art that the formulae I and II are intended to describe the structure of the present peptides in more convenient manner and their modifications fall within the scope of the present invention. For example, it would be obvious to those of skill in the art that peptides having reversed positions of the TGF-β1 derived sequence and the cell adhesion sequence in the formulae I and II, i.e., "cell adhesion sequence-Ile-Trp-Ser-Leu-Asp-Thr-Gln-Tyr (SEQ ID NO:1)" and "cell adhesion sequence-linker-Ile-Trp-Ser-Leu-Asp-Thr-Gln-Tyr (SEQ ID NO:1)" fall within the scope of this invention. Furthermore, peptides comprising additional amino acid residues (e.g., 1-2 residues) in the TGF-β1 derived sequence and/or the cell adhesion sequence would be encompassed by the present invention. For instance, where the cell adhesion sequence (Arg-Gly-Asp (SEQ ID NO:3)) contains additional Ser residue at its C-terminal, it could be also encompassed by the present invention.

The present peptides exhibits excellent skin whitening effects and anti-angiogenic activities as well as plausible stability to physiochemical factors such as heat, acid and alkali. Therefore, the peptides of this invention having significant long-term storage stability can be advantageously applied to products requiring long-term storage such as drugs, quasi-drugs, cosmetics and tooth/mouth cleaning or caring products.

In another aspect of this invention, there is provided an anti-angiogenic composition comprising the TGFP-CAP peptide of the present invention described above.

In still another aspect of this invention, there is provided a method for preventing or treating angiogenesis-associated diseases, which comprises administering to a subject a pharmaceutical composition comprising (a) a therapeutically effective amount of the TGFP-CAP peptide of the present invention and (b) a pharmaceutically acceptable carrier.

In further aspect of this invention, there is provided a use of the TGFP-CAP peptide of the present invention for manufacturing a medicament for preventing or treating angiogenesis-associated diseases.

Since the present composition comprises the TGFP-CAP peptide as active ingredients, the common descriptions between them are omitted so as to avoid undue redundancy leading to the complexity of this specification.

The peptides used as active ingredients exhibit excellent anti-angiogenic activities described in Examples. The present composition is useful in prevention, amelioration or treatment of diseases or conditions caused by excess angiogenesis.

The term used herein "angiogenesis-associated diseases" means diseases, disorders or conditions caused by unregulated growth of blood vessels.

According to a preferred embodiment, the present composition is used to prevent or treat cancers, diabetic retinopathy, retinopathy of prematurity, corneal graft rejection, neovascular glaucoma, rubeosis, proliferative retinopathy, psoriasis, hemophiliac joints, capillary proliferation within atherosclerotic plaques, keloids, wound granulation, stenosis, rheumatoid arthritis, bone arthritis, autoimmune diseases, Crohn's disease, restenosis, atherosclerosis, cat scratch disease, intestinal adhesions, ulcers, glomerulonephritis, diabetic nephropathy, malignant nephrosclerosis, thrombotic microangiopathy, organ transplant rejection, glomerulonephropathy, diabetic mellitus, inflammation or neurodegenerative diseases. Most preferably, the present composition is used to prevent, ameliorate or treat cancers. In particular, the present composition is very effective in treatment of skin cancer.

In another aspect of this invention, there is provided a skin whitening composition comprising the TGFP-CAP peptide of the present invention as active ingredients.

In still another aspect of this invention, there is provided a method for skin whitening, which comprises administering to a subject a composition comprising the TGFP-CAP peptide of the present invention.

In further aspect of this invention, there is provided a use of the TGFP-CAP peptide of the present invention for manufacturing a composition for skin whitening.

The TGFP-CAP peptide of the present invention prevents effectively melanin generation in skin to show whitening effects. The skin whitening composition of this invention permits to bright skin color, equalize skin tone and remove skin pigments and dark spots.

The present composition may be prepared as a pharmaceutical or cosmetic composition.

According to a preferred embodiment, the composition is a pharmaceutical composition comprising (a) a therapeutically effective amount of the present peptide; and (b) a pharmaceutically acceptable carrier.

The term used herein "therapeutically effective amount" refers to an amount enough to show and accomplish efficacies and activities of the peptide of this invention.

The pharmaceutically acceptable carrier contained in the pharmaceutical composition of the present invention, which is commonly used in pharmaceutical formulations, but is not limited to, includes lactose, dextrose, sucrose, sorbitol, mannitol, starch, rubber arable, potassium phosphate, arginate, gelatin, potassium silicate, microcrystalline cellulose, polyvinylpyrrolidone, cellulose, water, syrups, methylcellulose, methylhydroxy benzoate, propylhydroxy benzoate, talc, magnesium stearate, and mineral oils. The pharmaceutical composition according to the present invention may further include a lubricant, a humectant, a sweetener, a flavoring agent, an emulsifier, a suspending agent, and a preservative. Details of suitable pharmaceutically acceptable carriers and formulations can be found in *Remington's Pharmaceutical Sciences* (19th ed., 1995), which is incorporated herein by reference.

The pharmaceutical composition according to the present invention may be administered orally or parenterally, and preferably, parenterally, e.g., by intravenous, intraperitoneal, intramuscular, subcutaneous, transdermal or local administration.

A suitable dosage amount of the pharmaceutical composition of the present invention may vary depending on pharmaceutical formulation methods, administration methods, the patient's age, body weight, sex, pathogenic state, diet, administration time, administration route, an excretion rate and sensitivity for a used pharmaceutical composition. Preferably, the pharmaceutical composition of the present invention may be administered with a daily dosage of 0.0001-100 μg.

According to the conventional techniques known to those skilled in the art, the pharmaceutical composition according to the present invention may be formulated with pharmaceutically acceptable carrier and/or vehicle as described above, finally providing several forms a unit dose form and a multi-dose form. Non-limiting examples of the formulations include, but not limited to, a solution, a suspension or an emulsion in oil or aqueous medium, an extract, an elixir, a powder, a granule, a tablet and a capsule, and may further comprise a dispersion agent or a stabilizer.

According to a preferred embodiment, the composition is a cosmetic composition comprising (a) a cosmetically effective amount of the present peptide; and (b) a cosmetically acceptable carrier.

The term used herein "cosmetically effective amount" refers to an amount enough to accomplish efficacies on improvements in skin conditions described hereinabove.

The cosmetic compositions of this invention may be formulated in a wide variety of forms, for example, including a solution, a suspension, an emulsion, a paste, an ointment, a gel, a cream, a lotion, a powder, a soap, a surfactant-containing cleanser, an oil, a powder foundation, an emulsion foundation, a wax foundation and a spray. Specifically, the cosmetic compositions of this invention may be formulated in the form of skin softener, nutrient liquid, nutrient cream, massage cream, essence, eye cream, cleansing cream, cleansing foam, cleansing water, pack, spray or powder.

Where the cosmetic composition is in the form of paste, cream or gel, it may comprise animal and vegetable fats, waxes, paraffins, starch, tragacanth, cellulose derivatives, polyethylene glycols, silicones, bentonites, silica, talc, zinc oxide or mixtures of these substances.

In the formulation of powder or spray, it may comprise lactose, talc, silica, aluminum hydroxide, calcium silicate, polyamide powder and mixtures of these substances. Spray may additionally comprise the customary propellants, for example, chlorofluorohydrocarbons, propane/butane or dimethyl ether.

The formulation of solution and emulsion may comprise solvent, solubilizer and emulsifier, for example water, ethanol, isopropanol, ethyl carbonate, ethyl acetate, benzyl alcohol, benzyl benzoate, propylene glycol, 1,3-butylglycol, oils, glycerol fatty esters, polyethylene glycol and fatty acid esters of sorbitan.

The formulation of suspension may comprise liquid diluents, for example water, ethanol or propylene glycol, suspending agents, for example ethoxylated isostearyl alcohols, polyoxyethylene sorbitol esters and poly oxyethylene sorbitan esters, micocrystalline cellulose, aluminum metahydroxide, bentonite, agar and tragacanth or mixtures of these substances.

The formulation of cleansing compositions with surfactant may comprise aliphatic alcohol sulfate, aliphatic alcohol ether sulfate, sulfosucinnate monoester, isothionate, imidazolium derivatives, methyltaurate, sarcosinate, fatty acid amide ether sulfate, alkyl amido betain, aliphatic alcohol, fatty acid glyceride, fatty acid diethanolamide, vegetable oil, lanoline derivatives, ethoxylated glycerol fatty acid ester or mixtures of these ingredients.

Furthermore, the cosmetic compositions of this invention may contain auxiliaries as well as peptides as active ingredients and carriers. The non-limiting examples of auxiliaries include preservatives, antioxidants, stabilizers, solubilizers, vitamins, colorants, odor improvers or mixtures of these substances.

The features and advantages of the present invention are summarized as follows:

(i) The TGFP-CAP peptide of the present invention exhibits excellent anti-angiogenic activity.

(ii) The TGFP-CAP peptide of the present invention prevents effectively melanin generation in skin to have skin whitening effects.

(iii) The present peptide shows much higher stability and permeability to skin than natural-occurring TGF-β1.

(iv) The plausible activities and safety of the present peptide afore-described enable advantageously to application to drugs, quasi-drugs and cosmetics.

Figure 1:
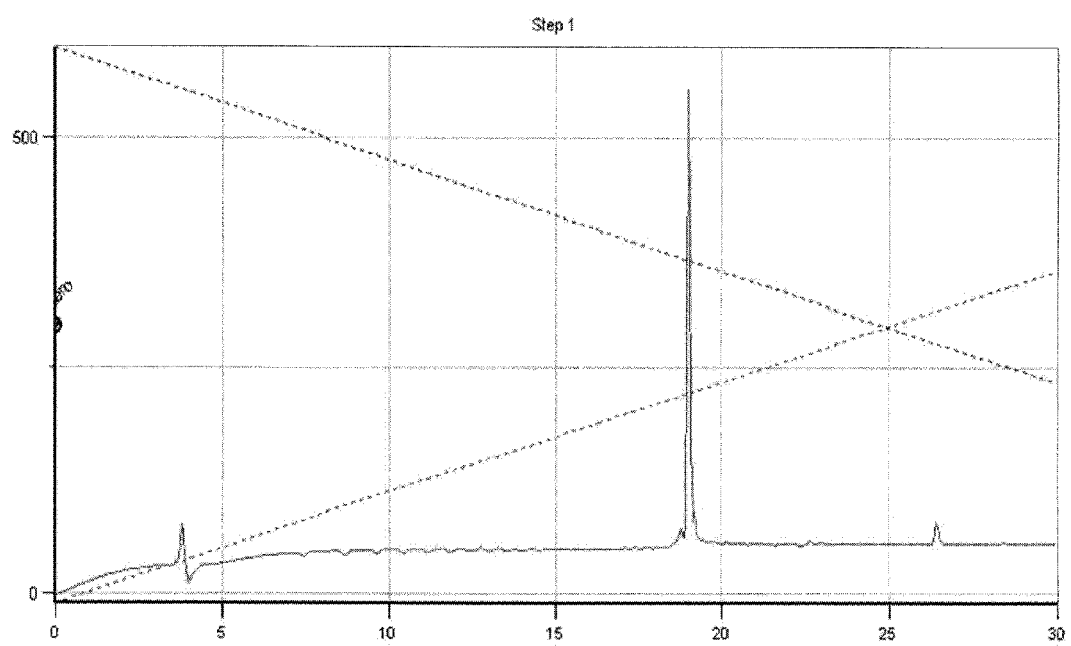
FIG. 1 represents results of high performance liquid chromatography analysis of the tridecapeptide prepared in Example.

The present invention will now be described in further detail by examples. It would be obvious to those skilled in the art that these examples are intended to be more concretely illustrative and the scope of the present invention as set forth in the appended claims is not limited to or by the examples.

EXAMPLES

Example 1

Synthesis of NH$_2$-Ile-Trp-Ser-Leu-Asp-Thr-Gln-Tyr-Gly(n)-Arg-Gly-Asp-OH (SEQ ID NO:32)

700 mg of chloro trityl chloride resin (CTL resin, Nova Biochem Cat No. 01-64-0021) were introduced into a reactor, to which 10 ml of methylene chloride (MC) were added, followed by agitation for 3 min. After removing solution, 10 ml of dimethylformamide (DMF) were added to the resultant and then agitation was carried out for 3 min, after which the solvent was removed. 10 ml of dichloromethane solution were added to the reactor and 200 mmole of Fmoc-Asp(otbu)-OH and 400 mmole of DIEA were then added to the reactor, after which the mixture was dissolved by agitation and reaction was then undertaken with agitating for 1 hr. After washing, the resin was reacted with a mixture of methanol and DIEA (2:1) in MC for 10 min, and then washed with excess of MC/DMF (1:1). After removing solution, 10 ml of DMF were added to the resultant and agitation was performed for 3 min, followed by removing the solvent. 10 ml of a deprotection solution (20% piperidine/DMF) were added to the reactor and agitation for 10 min at room temperature and solution removal were performed. After adding the same volume of the deprotection solution, the reaction was undertaken for 10 min and solution was removed, followed by washing sequentially with DMF, MC and DMF to yield Asp-CTL resins. 10 ml of DMF solution was added to a new reactor and then 200 mmole of Fmoc-Gly-OH (Novabiochem, USA), 200 mmole of HoBt and 200 mmole of Bop were added, followed by agitation for solubilization. 400 mmole of DIEA was added to the reactor and agitation was carried out to dissolve all solid contents. The dissolved amino acid solution was introduced into the reactor containing the deprotected resin and reaction was undertaken with agitating for 1 hr at room temperature. Following the removal of the reaction solution, the resultant was agitated three times with DMF solution to remove unreacted residuals. A small amount of the reacted resin was taken to evaluate extent of reactions by Ninhydrine test. Using the deprotection solution, the deprotection was performed twice in the same manner as described above to yield Gly-Asp (tBu)-CTL resins. After washing with DMF and MC, Ninhydrine test was carried out and the attachments of amino acids were performed as described above. Based on the amino acid sequence designed by the present inventors, Fmoc-Arg(pbf), Fmoc-Gly(n times), Fmoc-Tyr(tBu), Fmoc-Gln(trt), Fmoc-Thr(tBu), Fmoc-Asp(otbu), Fmoc-Leu, Fmoc-Ser(tBu), Fmoc-Trp(boc) and Fmoc-Ile were sequentially attached to resins. Gly residues were introduced in the number of 2-6, thereby producing all five types of peptidyl resins. The prepared peptidyl resin was deprotected for Fmoc removal, washed three times with DMF, MC and methanol, respectively and dried under nitrogen atmosphere, after which it was vacuum-dried under $P_2O_5$, finally giving peptidyl resins of interest. The dried peptidyl resin was reacted with 30 ml of a leaving solution [containing 81.5% trifluoroacetic acid (TFA), 5% distilled water, 5% thioanisole, 5% phenol, 2.5% EDTA and 1% TIS] for 2 hr at room temperature upon intermittent agitating. The resin was filtered and washed with a small volume of TFA solution, after which the filtrate was combined with the mother liquor. After distillation under reduced pressure to reduce the total volume by two, the precipitation was induced using 50 ml of cold ether and the formed precipitates were collected by centrifugation, followed by washing twice with cold ether. After removing the mother liquor, the resultant was dried under nitrogen atmosphere to provide 0.93 g of unpurified five peptides represented by $NH_2$-Ile-Trp-Ser-Leu-Asp-Thr-Gln-Tyr-Gly(n)-Arg-Gly-Asp-OH (SEQ IS NO:32). Among them, $NH_2$-Ile-Trp-Ser-Leu-Asp-Thr-Gln-Tyr-Gly-Gly-Arg-Gly-Asp-OH (SEQ ID NO:2) was obtained in the amount of about 0.87 g and its molecular weight was measured as 1467.9 (theoretical MW 1467.5) using a mass analyzer (Perseptive Pioneer DE-STR ABI, USA).

Example 2

Stability Analysis of Tridecapeptide

Figure 2:
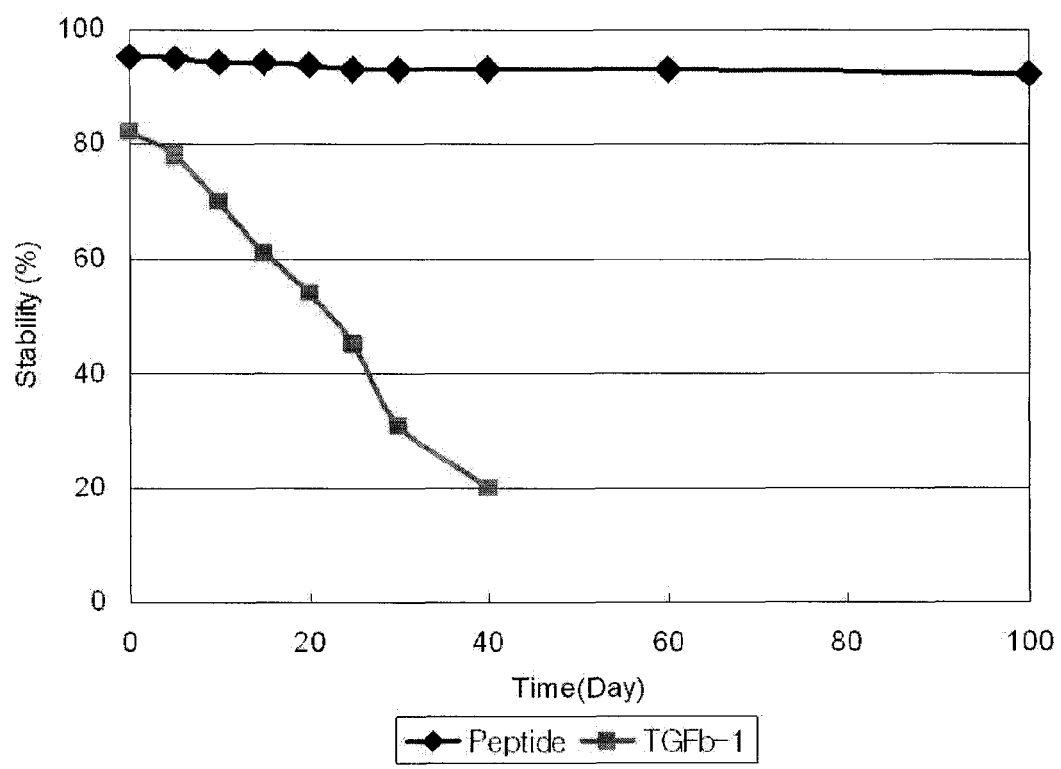
FIG. 2 represents analysis results of stability of the tridecapeptide prepared in Example. The term "Peptide" denotes the present peptide comprising two Gly residues as a linker synthesized in Example 1. The term "TGFb-1" denotes TGF-β1.

To evaluate stability of the purified tridecapeptide, $NH_2$-Ile-Trp-Ser-Leu-Asp-Thr-Gln-Tyr-Gly-Gly-Arg-Gly-Asp-OH, it was dissolved in 50 mM Tris-HCl (pH 8.0) to a concentration of 10 μg/ml. A recombinant TGF-β1 (Sigma) produced by *E. coli* was prepared as a control in the same buffer to a concentration of 1 μg/ml. The prepared solutions were introduced into glass vials and kept to stand at 37° C. Afterwards, the solutions were taken on days 0, 1, 10, 25, 50, 75 and 100 and subjected to a MTT assay (Scudiero, D. A., et al. *Cancer Res.* 48:4827-4833 (1988)) using NIH-3T3 cells (Korean Cell Line Bank) for determining their remaining activity (FIG. 2). The results were given as relative values to the activity (100%) of sample taken on day 0.

As represented in FIG. 2, the activity of the recombinant TGF-β1 was sharply decreased with the lapse of time. In contrast, the activity of the present tridecapeptide was shown not to be decreased over time.

Example 3

Preparation of Nano Peptides 50 mg of the tridecapeptide synthesized was dissolved in 500 ml of distilled water. The peptide solution was mixed with 5 g lecithin, 0.3 ml sodium oleate, 50 ml ethanol and a small amount of oils and its volume was adjusted with distilled water to 1 L. The resulting solution was subjected to a microfluidizer under high pressure for emulsification, thereby providing nanosomes having 100-nm size. The nanosomes were prepared to have a final concentration of about 50 ppm and used as ingredients for cosmetics.

Formulation Example 1

Skin Softener

A skin softener containing nanosomes of the tridecapeptide prepared in Example 3 was formulated according to the following composition.

TABLE 1

| Ingredients | Content (wt %) |
| --- | --- |
| Tri-decapeptide | 0.001 |
| 1,3-butylene glycol | 6.0 |
| Glycerine | 4.0 |
| PEG 1500 | 1.0 |
| Sodium hyaluronate | 1.0 |
| Polysorbate 20 | 0.5 |
| Ethanol | 8.0 |
| Preservative, pigment | Proper amount |
| Benzophenone-9 | 0.05 |
| Perfume | Minute amount |
| Distilled water | Residual amount |
| Total | 100 |

Formulation Example 2

Nutrient Cream

A nutrient cream containing nanosomes of the tridecapeptide prepared in Example 3 was formulated according to the following composition.

TABLE 2

| Ingredients | Content (wt %) |
| --- | --- |
| Tri-decapeptide | 0.001 |
| Meadowfoam oil | 3.0 |
| Cetearylalcohol | 1.5 |
| Stearic acid | 1.5 |
| Glyceryl stearate | 1.5 |
| Liquid paraffin | 10.0 |
| Wax | 2.0 |
| Polysorbate 60 | 0.6 |
| Sorbitan sesquiolate | 2.5 |
| Squalane | 3.0 |
| 1,3-butylene glycol | 3.0 |
| Glycerine | 5.0 |
| Triethanol amine | 0.5 |
| Tocopheryl acetate | 0.5 |
| Preservative, pigments | Proper amount |
| Perfume | Proper amount |
| Distilled water | Residual amount |
| Total | 100 |

Formulation Example 3

Nutrient Liquid

A nutrient liquid containing nanosomes of the tridecapeptide prepared in Example 3 was formulated according to the following composition.

TABLE 3

| Ingredients | Content (wt %) |
|---|---|
| Tri-decapeptide | 0.002 |
| 1,3-butylene glycol | 4.0 |
| Glycerine | 4.0 |
| Cetearyl alcohol | 0.8 |
| Glyceryl stearate | 1.0 |
| Triethanol amine | 0.13 |
| Tocopheryl acetate | 0.3 |
| Liquid paraffin | 5.0 |
| Squalane | 3.0 |
| Makadamianut oil | 2.0 |
| Polysorbate 60 | 1.5 |
| Sorbitan sesquiolate | 0.5 |
| Carboxyvinyl polymer | 1.0 |
| Preservative, pigments | Proper amount |
| Perfume | Proper amount |
| Distilled water | Residual amount |
| Total | 100 |

Formulation Example 4

Essence

An essence containing nanosomes of the tridecapeptide prepared in Example 3 was formulated according to the following composition.

TABLE 4

| Ingredients | Content (wt %) |
|---|---|
| Tri-decapeptide | 0.005 |
| Glycerine | 10.0 |
| 1,3-butylene glycol | 5.0 |
| PEG 1500 | 2.0 |
| Allantoin | 0.1 |
| DL-panthenol | 0.3 |
| EDTA-2Na | 0.02 |
| Hydroxyethyl cellulose | 0.1 |
| Sodium hyaluronate | 8.0 |
| Carboxyvinyl polymer | 0.2 |
| Triethanol amine | 0.18 |
| Octyldodeceth-16 | 0.4 |
| Ethanol | 6.0 |
| Perfume, preservative, pigments | Proper amount |
| Distilled water | Residual amount |
| Total | 100 |

Example 4

Melanin Pigment Decrease by Tridecapeptide

The tridecapeptide synthesized in Example 1 was analyzed to decrease levels of melanin pigment. Mice melanocytes cultured were incubated with α-MSH (melanocyte stimulating hormone/Sigma) and then with the tridecapeptide in the determined concentrations to measure inhibition effects on melanin generation. Mice melanocytes were originated from C57BL/6 mice and cultured in DMEM (Dulbecco's modified Eagle's media) containing 10% fetal bovine serum at 37° C. under 5% $CO_2$ conditions. Cells were cultured in a density of $1 \times 10^5$ cells/well and their adhesion to culture plates was observed. Then, cells were incubated with materials to be tested for 3 days. The tested materials were prepared in such a manner that components indicated in Table 5 were dissolved in medium and diluted with a mixed solvent of propylene glycol:ethanol:distilled water (5:3:2). Following removal of medium, cells were washed with PBS and treated with 1 N sodium hydroxide. The resultants were analyzed to measure their absorbance values at 400 nm. The measured inhibition in melanin generation was shown in FIG. 3 (Dooley method).

TABLE 5

| No. | Compositions |
|---|---|
| A | Negative control |
| B | α-MSH 200 ng/ml |
| C | α-MSH 200 ng/ml + TGFβ-1 10 ng/ml |
| D | α-MSH 200 ng/ml + peptide 10 ng/ml |
| E | α-MSH 200 ng/ml + peptide 100 ng/ml |
| F | α-MSH 200 ng/ml + peptide 10 μg/ml |
| G | α-MSH 200 ng/ml + peptide 30 μg/ml |

Figure 3:
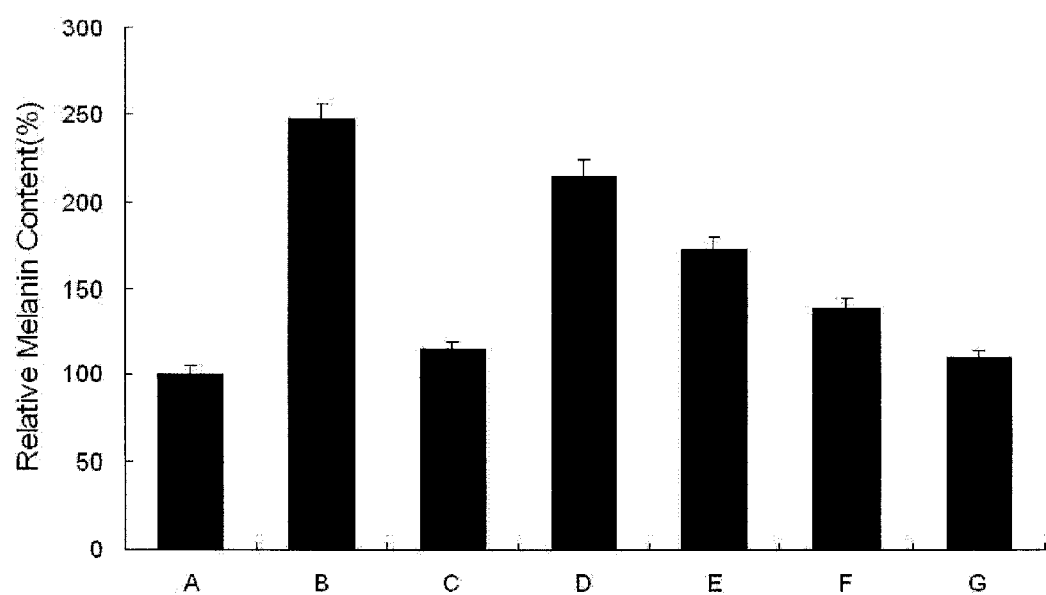
FIG. 3 represents dose-dependent inhibitory effects of the present tridecapeptide on melanin generation by α-MSH in B16F10 melanoma cells.

As represented in FIG. 3, the group incubated with only α-MSH shows highly elevated level of melanin production. In contrast, the group incubated with the tridecapeptide represents decreased melanin content in a concentration dependent manner. The tridecapeptide treatment gives rise to decrease in melanin level similar to that of no α-MSH treatment. These results urge us to reason that the tridecapeptide can inhibit activities of melanin-generating causes and therefore bright skin tones.

Example 5

Inhibition of Tyrosinase Activity by Tridecapeptide

The tridecapeptide synthesized in Example 1 was analyzed to decrease levels of melanin pigment. B16F10 cells (Korean Cell Line Bank) were plated in a density of $1 \times 10^5$ cells/well and cultured in DMEM (Sigma) for 3 days at 37° C. under 5% $CO_2$ conditions. After cell adhesion was observed, medium was changed with a fresh medium containing 2% serum. Cells were incubated with tested materials in determined concentrations for 4 days at 37° C. under 5% $CO_2$ conditions. The tested materials were prepared in such a manner that components indicated in Table 6 were dissolved in medium and diluted with a mixed solvent of propylene glycol:ethanol:distilled water (5:3:2).

TABLE 6

| No. | Compositions |
|---|---|
| A | Negative control |
| B | α-MSH 200 ng/ml |
| C | α-MSH 200 ng/ml + TGFβ-1 10 ng/ml |
| D | α-MSH 200 ng/ml + peptide 10 ng/ml |
| E | α-MSH 200 ng/ml + peptide 100 ng/ml |
| F | α-MSH 200 ng/ml + peptide 10 μg/ml |
| G | α-MSH 200 ng/ml + peptide 30 μg/ml |

Afterwards, cells were harvested and treated with a lysis buffer containing sodiumdodecylsulfate (Sigma) and Triton X-100 (Sigma) to extract intracellular proteins. The extracted proteins were quantitated by the BCA method. For each experiment group, 90 μl of protein solution and 10 μl of L-DOPA (Sigma) were added and reacted for 30 min. The resultants were analyzed to measure their absorbance values at 405 nm for evaluating tyrosinase activities.

Figure 4:
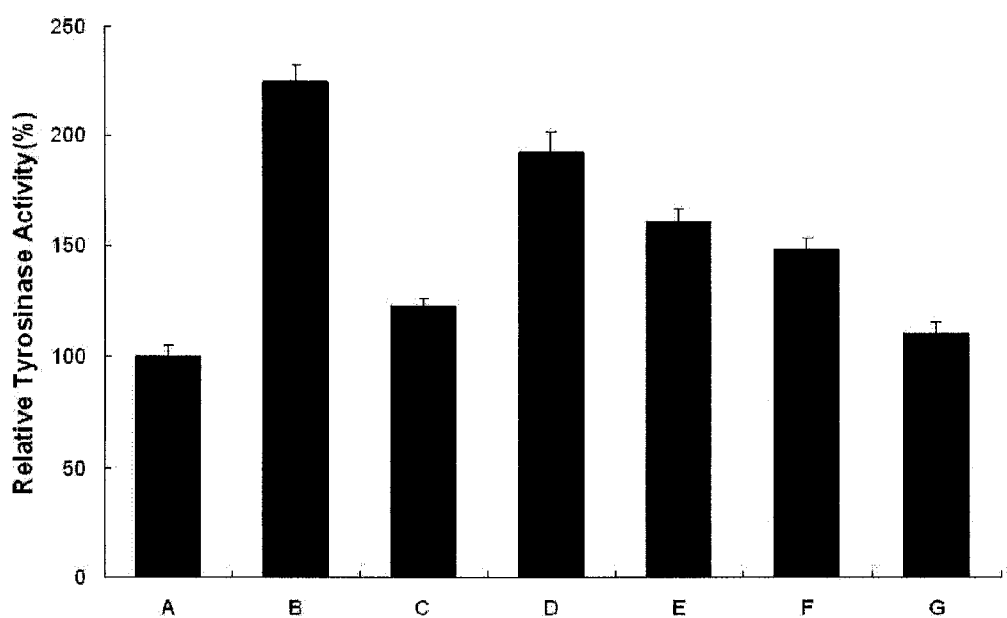
FIG. 4 represents inhibitory effects of the present tridecapeptide on tyrosinase activity in B16F10 melanoma cells. TGF-β1 was used as controls.

As represented in FIG. 4, the group treated with only α-MSH shows highly elevated level of tyrosinase activity. In contrast, the group treated with either TGF-β1 or the tridecapeptide represents relatively reduced tyrosinase activity in a dose dependent manner. The tridecapeptide treatment gives rise to decrease in tyrosinase activity similar to that of no α-MSH treatment. These results urge us to reason that the tridecapeptide can negate tyrosinase activation-causing effects and therefore bright skin tones. In addition, it would be understood that the tridecapeptide of this invention has its action mechanism identical to that of TGF-β1.

Example 6

ERK Phosphorylation by Tridecapeptide

To reveal skin whitening effects of the tridecapeptide synthesized in Example 1 and transforming growth factor, the activation of ERK was inhibited with PD98059 (Sigma) and then its inhibitory influence was evaluated after peptide treatment. B16F10 cells were seeded in 6-well culture dishes in a density of $1\times10^5$ cells/well and cultured in DMEM for 3 days at 37° C. under 5% $CO_2$ conditions. After cell adhesion was observed, medium was changed with a fresh medium containing 2% serum. The negative control was not subject to any treatment. Cells plated in other two culture dishes were incubated with either 1 ng/ml transforming growth factor or 30 μg/ml tridecapeptide. In addition, cells cultured in other three dishes as a positive control were incubated with 10 μM PD98059 to inhibit ERK phosphorylation. Among them, cells contained in two dishes were incubated for 4 days with either 1 ng/ml transforming growth factor or 30 μg/ml tridecapeptide after 1-hr PD98059 treatment and their morphology was observed under microscopes.

Figure 5:
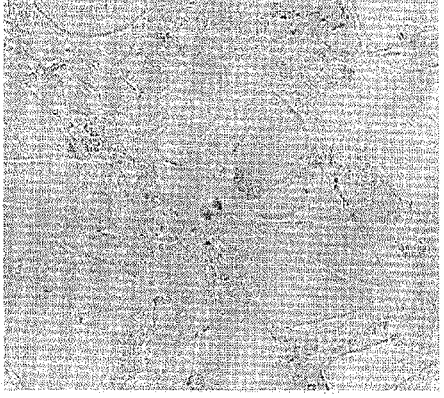
FIG. 5 is a microscope image representing influence of the present tridecapeptide on activation of ERK 1/2 in B16F10 melanoma cells. The number of melanosomes was evaluated. TGF-β1 was used as controls. The term "TGP2" denotes the present peptide comprising two Gly residues as a linker synthesized in Example 1. The term "TGFb-1" denotes TGF-β1.
Figure 5:
Figure 5:
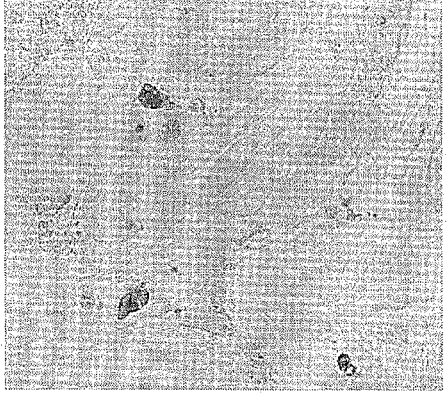
Figure 5:
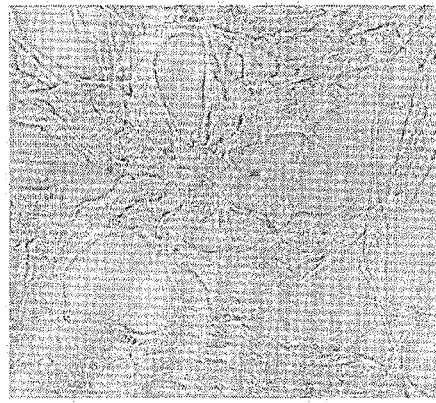

As shown in FIG. 5, cells incubated with PD98059 were shown to have a large number of darkish pigments by induced melanosomes. In contrast, cells incubated with either transforming growth factor or tridecapeptide along with PD98059 were observed to have significantly reduced melanosome number, demonstrating that the tridecapeptide of this invention can induce ERK phosphorylation (Phospo-ERK) as TGF-β1 to prevent melanosome formation.

Figure 6:
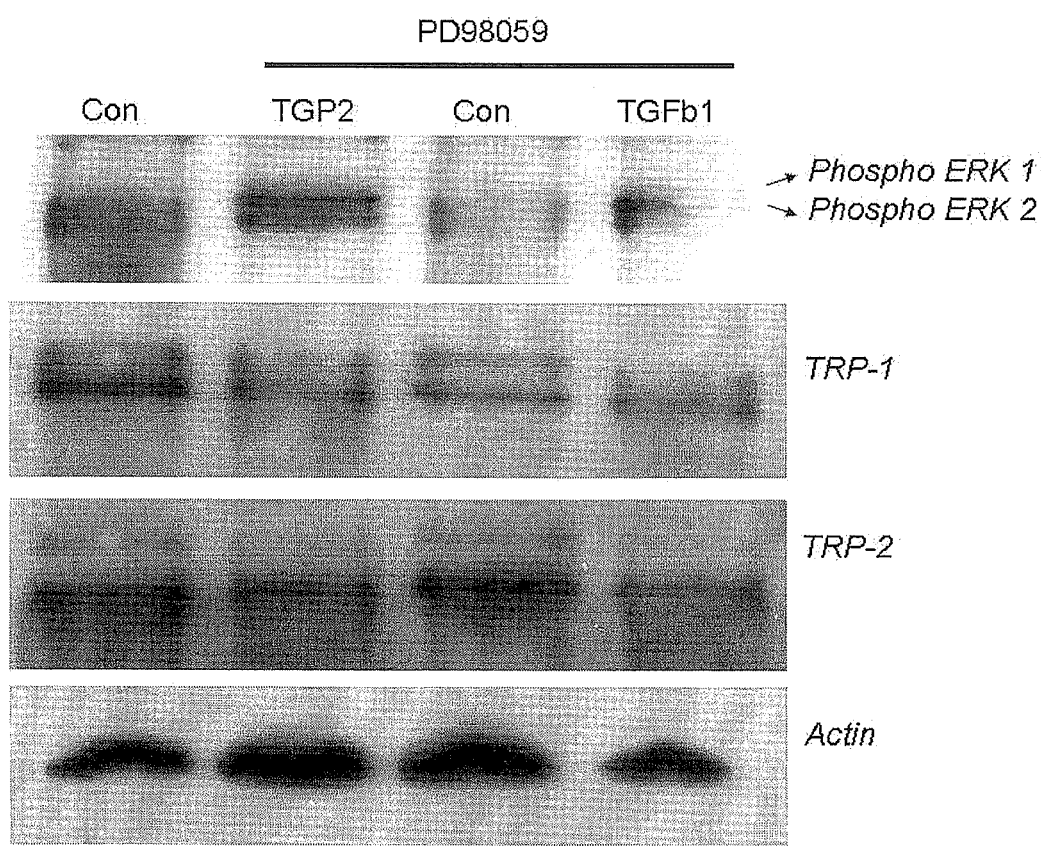
FIG. 6 is Western blotting analysis results verifying that the present tridecapeptide restores phosphorylation of ERK 1/2 inhibited by PD98059 in B16F10 melanoma cells.

Furthermore, to clearly verify the influence of TGF-β1 and tridecapeptide on signaling events, melanoma cells were cultured as described above and then incubated simultaneously with 10 μM PD98059 and 30 μg/ml tridecapeptide. Proteins from cell extracts were prepared and developed on SDS-PAGE, followed by electro-transferring to PVDF (polyvinylidene difluoride) membrane (GE Health Care). Afterwards, the PVDF membrane was incubated with Phospho ERK 1/2 antibodies (1/3000 diluted, Cell Signaling, USA) for 4 hr at room temperature. The PVDF membrane was washed with a washing buffer and incubated with HRP-conjugated anti-mouse IgG antibodies (1/5000 diluted, SantaCruz, USA). Then, it was washed twice with a washing buffer and incubated with ECL (enhanced chemilumineseance) solution (GE Health Care) (FIG. 6). In FIG. 6, among PD98059 treatment groups, the symbol "Con" is a group incubated with only 10 μM PD98059 and "TGFb1" is a group incubated with both 10 μM PD98059 and 10 ng/ml TGF-β1.

As represented in FIG. 6, the treatment of PD98059 was analyzed to greatly decrease levels of Phoshpo ERK 1 and ERK 2. In contrast, the treatment of either TGF-β1 or tridecapeptide gave rise to elevated levels of Phoshpo ERK 1 and ERK 2. Meanwhile, levels of TRP-1 (tyrosinase related protein-1) and TRP-2 were increased by PD98059 and decreased by either TGF-β1 or tridecapeptide. These results lead us to conclude that the tridecapeptide of this invention can affect ERK-involved signaling events in the same manner as TGF-β1.

Example 7

Inhibition of Growth of Transplanted Melanoma Cells by Tridecapeptide

Normal 5 week-aged male Balb/C mice (Central Lab Animal Inc, Korea) were removed of its back hairs and $2\times10^6$ B16F10 melanoma cells (Korean Cell Line Bank) were xenotransplanted into each of two transplanted portions. After mice were maintained for 3 days upon normal feeding, transplanted portions with melanoma cells were observed to be swelled. One of transplanted portions as control was administered with PBS and the other portion was administered twice a day with about 100 μg of the tridecapeptide.

Figure 7:
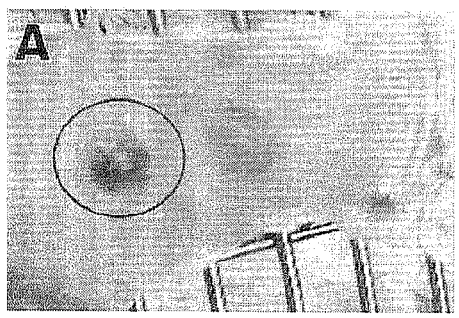
FIG. 7 is a photograph showing that the size of melanoma tumors xenotransplanted into mice was reduced by the present tridecapeptide.
Figure 7:
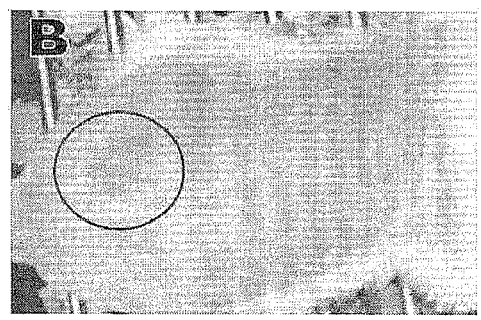
Figure 7:
Figure 7:
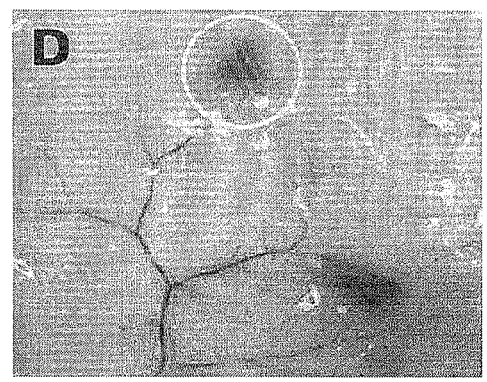
Figure 8:
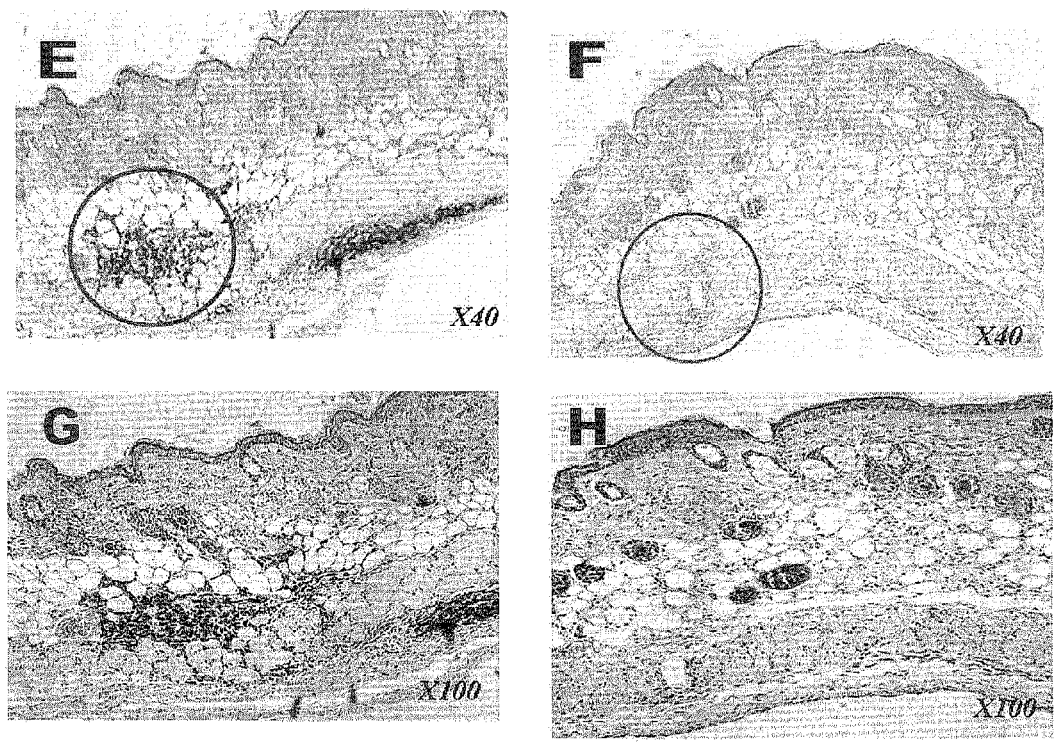
FIG. 8 demonstrates that the present tridecapeptide inhibits metastasis of melanoma xenotransplanted into mice.

FIG. 7 is photographs of tumor sites of mice after 1 week of administration with the tridecapeptide. Tumor regression was clearly observed at the site administered with the tridecapeptide. In addition, mice were sacrificed and tumoric sites were analyzed. As a result, it was observed that both tumor metastasis and angiogenesis were inhibited. The tumor sites were paraffinized to obtain thin slices and then stained with hematoxylin and eosin, as represented in FIG. 8. It was observed that the production of melanoma cells in tissues was significantly decreased.

Example 8

Cytotoxicity Test of Tridecapeptide

Figure 9:
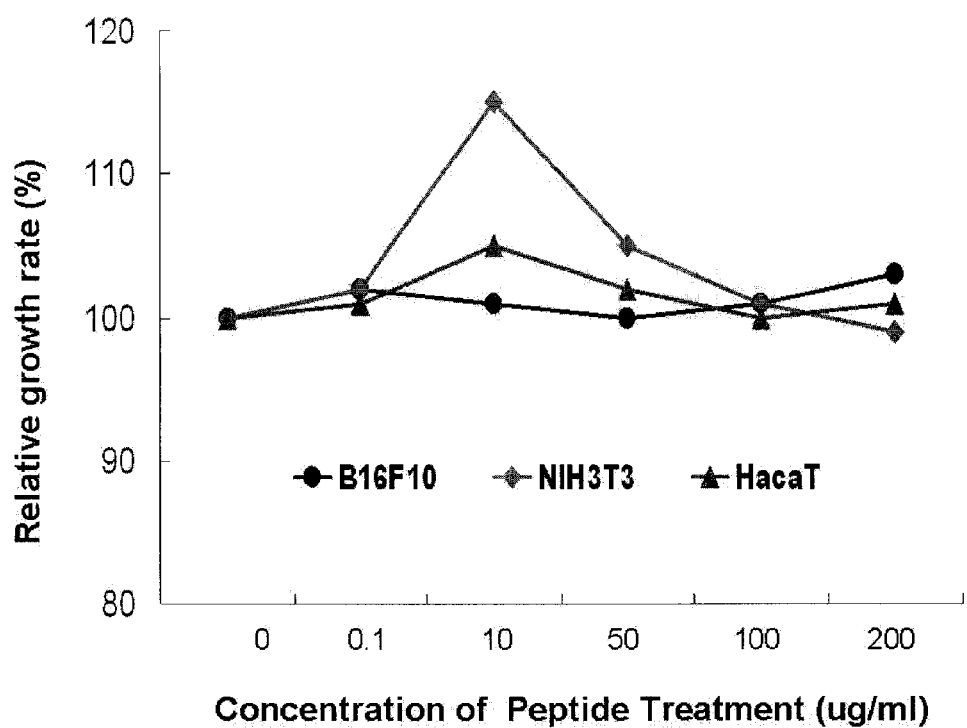
FIG. 9 represents cytotoxicity analysis results of the present tridecapeptide synthesized in Example.

To verify cytotoxicity of peptides of this invention on keratinocytes, fibroblasts and melanoma cells, SRB (Sulforhodamine B) colorimetric assay was carried out using HaCaT, NIH3T3 and B16F10 cells according to Rizzino et al method (Rizzino, et al. *Cancer Res.*, 48:4266 (1988)). HaCaT, NIH3T3 or B16F10 cells (Korean Cell Line Bank) were cultured in 250 ml-flasks containing EMEM (Eagle's minimal essential media, Gibco, U.S.A.) supplemented with 100% FBS (fetal bovine serum). Cells cultured were treated with 0.25% trypsin solution to detach cells from the bottom of culture flasks and centrifuged to collect cell pellets. Cells were resuspended in EMEM not containing FBS, its aliquot $(1\times10^5)$ cells was added to each well of 96-well plates and cultured under 7% $CO_2$ for 24 hr at 37° C. After 24-hr culture, the medium was changed with a fresh medium not containing serum and cells were incubated with the tridecapeptide (500 pg/ml, 10 ng/ml, 1 μg/ml, 100 μg/ml and 200 μg/ml) dissolved in 10% DMSO for 72 hr under the same conditions as described above. After removing supernatants, cells were washed once using PBS and incubated with SRB solution (Sigma). Cells were washed with PBS and observed under a microscope to find cell viability. In addition, absorbance at 590 nm was measured to analyze cell proliferation. As represented in FIG. 9, the decrease in cell number was not shown under microscope in all concentrations of the tridecapeptide. These results address that the peptide of the present invention induce little or no adverse effects on skin cells.

The TGFP-CAP peptide of the present invention exhibits excellent anti-angiogenic activity. In addition, the TGFP-CAP peptide of the present invention prevents effectively melanin generation in skin to have skin whitening effects. The present peptide shows much higher stability and permeability to skin than natural-occurring TGF-β1. Such plausible activities and safety of the present peptide enable advantageously to application to drugs, quasi-drugs and cosmetics.

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. A TGFP (transforming growth factor-beta peptide)CAP (cell adhesion peptide) peptide consisting of an amino acid sequence derived from TGF-β1(transforming growth factor-β1), a linker, and a cell adhesion sequence, wherein the TGFP-CAP peptide comprises said linker between the amino acid sequence derived from TGF-β1 and the cell adhesion sequence and the TGFP-CAP peptide is represented by the following formula II:

Ile-Trp-Ser-Leu-Asp-Thr-Gln-Tyr (SEQ ID NO:1)-Linker-Cell adhesion sequence (II)

wherein the linker consists of 2-10 Gly residues and the cell adhesion sequence is RGD(Arg-Gly-Asp(SEQ ID NO:3).

2. The TGFP-CAP peptide of claim 1, wherein the TGFP-CAP peptide is represented by the following formula III:

Ile-Trp-Ser-Leu-Asp-Thr-Gln-Tyr-Gly(n)-Arg-Gly-Asp (SEQ ID NO:32) (III)

wherein n is an integer of 2-8.

3. The TGFP-CAP peptide of claim 1, wherein the N-terminal of the peptide is protected with a protection group selected from the group consisting of acetyl group, fluorenyl methoxy carbonyl group, formyl group, palmitoyl group, myristyl group, and stearyl group.

4. A method for treating angiogenesis-associated diseases, which comprises administering to a subject a pharmaceutical composition comprising (a) a therapeutically effective amount of the peptide of claim 1 and (b) a pharmaceutically acceptable carrier.

5. The method of claim 4, wherein the angiogenesis-associated disease is cancers, diabetic retinopathy, retinopathy of prematurity, corneal graft rejection, neovascular glaucoma, rubeosis, proliferative retinopathy, psoriasis, hemophiliac joints, capillary proliferation within atherosclerotic plaques, keloids, wound granulation, stenosis, rheumatoid arthritis, bone arthritis, autoimmune diseases, Crohn's disease, restenosis, atherosclerosis, cat scratch disease, intestinal adhesions, ulcers, glomerulonephritis, diabetic nephropathy, malignant nephrosclerosis, thrombotic microangiopathy, organ transplant rejection, glomerulonephropathy, diabetic mellitus, inflammation or neurodegenerative diseases.

6. A method for skin whitening, which comprises administering to a subject a composition comprising the peptide of claim 1.

* * * * *